United States Patent [19]

Martel et al.

[11] 4,382,037
[45] May 3, 1983

[54] 3-FORMYL-4-METHYL-PENTANOIC ACIDS

[75] Inventors: Jacques Martel, Bondy; Jean Tessier, Vincennes; Jean-Pierre Demoute, Montreuil-sous-Bois, all of France

[73] Assignee: Roussel Uclaf, Paris, France

[21] Appl. No.: 246,170

[22] Filed: Mar. 23, 1981

[30] Foreign Application Priority Data

Mar. 28, 1980 [FR] France ............................ 80 06978

[51] Int. Cl.³ .......................................... C07C 147/06
[52] U.S. Cl. ................................ 260/465 F; 560/11; 562/429; 562/577
[58] Field of Search ....................... 562/429; 560/11; 260/465 F

[56] References Cited

U.S. PATENT DOCUMENTS

Re. 27,592 3/1973 Martel et al. ..................... 260/464

OTHER PUBLICATIONS

House, Modern Synthetic Reaction, p. 494 (1972).

Primary Examiner—Robert Gerstl
Attorney, Agent, or Firm—Hammond & Littell, Weissenberger and Muserlian

[57] ABSTRACT

Novel 3-formyl-4-methyl-pentanoic acid derivatives of the formula

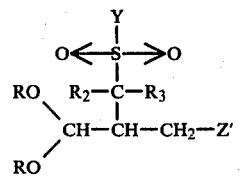

wherein Y is an aromatic group, $R_2$ and $R_3$ are individually alkyl of 1 to 4 carbon atoms or taken together with the carbon atom to which they are attached form a carbon homocycle of 3 to 6 carbon atoms, the Rs are alkyl of 1 to 6 carbon atoms or together form a polymethylene of 2 to 3 carbon atoms and Z' is selected from the group consisting of —COOH and Z and Z is selected from the group consisting of cyano and —COOR$_1$ wherein R$_1$ is alkyl of 1 to 6 carbon atoms and their preparation which are useful for the preparation of 3-formyl-4-$R_2R_3$-but-3-ene-1-oic acid which is an intermediate for the preparation of a compound of the formula

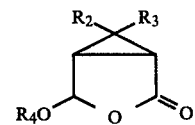

wherein R$_4$ is hydrogen or the remainder of an alcohol of the formula R$_1$OH by the process of copending, commonly assigned U.S. patent application No. 153,338 filed May 27, 1980.

3 Claims, No Drawings

3-FORMYL-4-METHYL-PENTANOIC ACIDS

STATE OF THE ART

Copending, commonly assigned U.S. patent application Ser. No. 153,338 filed May 27, 1980 describes the preparation of 3-formyl-4-methyl-pent-3-ene-1-oic acid by reacting a compound of the formula

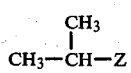

wherein Z is an electro-attractive group with a compound of the formula

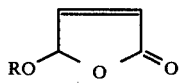

wherein R is the residue of an ROH alcohol to obtain a compound of the formula

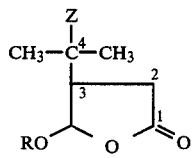

and treating the latter with a basic agent.

OBJECTS OF THE INVENTION

It is an object of the invention to provide the novel compounds of formula I and a novel process for their preparation.

It is another object of the invention to provide a novel process for the preparation of a substituted 3-formyl-but-3-ene-1-oic acid.

These and other objects and advantages of the invention will become obvious from the following detailed description.

THE INVENTION

The novel compound of the invention are 3-formyl-4-methyl-pentanoic acid derivatives of the formula

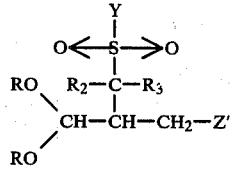

wherein Y is an aromatic group, $R_2$ and $R_3$ are individually alkyl of 1 to 4 carbon atoms or taken together with the carbon atom to which they are attached form a carbon homocycle of 3 to 6 carbon atoms, the Rs are alkyl of 1 to 6 carbon atoms or together form a polymethylene of 2 to 3 carbon atoms and Z' is selected from the group consisting of —COOH and Z and Z is selected from the group consisting of cyano and —COOR$_1$ wherein R$_1$ is alkyl of 1 to 6 carbon atoms.

Examples of suitable substituents of formula I for Y are aromatic groups such as phenyl, xylyl and preferably tolyl, for $R_2$ and $R_3$ are alkyl of 1 to 4 carbon atoms such as methyl, ethyl, propyl, isopropyl, butyl, sec.-butyl and tert.-butyl or taken together with the carbon atom to which they are attached form a carbon homocycle such as cyclopropyl, cyclobutyl, cyclopentyl and cyclohexyl. Examples of R are alkyl of 1 to 6 carbon atoms such as methyl, ethyl, propyl or butyl or taken together with the oxygen atoms form ethylenedioxy or trimethylenedioxy. Examples of $R_1$ are methyl, ethyl, propyl, isopropyl, butyl, sec.-butyl and tert.-butyl.

Among the preferred compounds of formula I are those of the formulae

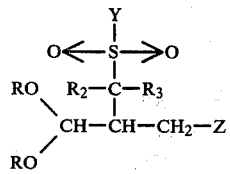

wherein Y, Z, R, $R_2$ and $R_3$ have the above definitions and

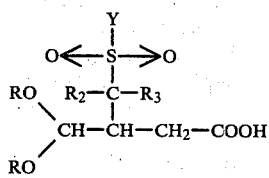

wherein Y, R, $R_2$ and $R_3$ have the above definitions.

The novel process of the invention for the preparation of a compound of formula I comprises reacting a compound of the formula

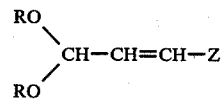

in the presence of a strong base in a polar solvent with a sulfone of the formula

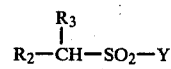

wherein R, Z, $R_2$, $R_3$ and Y have the above definitions to obtain the corresponding compound of formula $I_A$ which when Z is —COOR$_1$ may be reacted with a basic agent capable of saponifying the ester group to obtain the corresponding compound of formula $I_B$ or when Z is —CN, reacting the compound of formula $I_A$ with a hydrolysis agent capable of changing the —CN to an acid to obtain the corresponding acid of formula $I_B$.

In a preferred mode of the process of the invention, the strong base present during the reaction of the compounds of formulae II and III is selected from the group consisting of alkali metal alcoholates, alkali metal hydrides, alkali metal amides, phenyllithium and alkyllithium and the polar solvent is selected from the group consisting of dimethylsulfoxide, dimethoxyethane, dimethylformamide, tetrahydrofuran, hexamethylphosphorotriamide and mixtures thereof with monocyclic aromatic hydrocarbons or cycloalkanes and mixtures of the said solvents.

The preferred basic agent to saponify the group —COOR₁ is an alkali metal hydroxide in an aqueous alcohol solvent and the hydrolysis agent for the cyano group of the compound of formula $I_A$ is preferably an alkali metal hydroxide in aqueous alcohol but it is used in a more concentrated solution for a longer period of time than the ester hydrolysis.

The novel process of the invention for the preparation of a 3-formyl-4-R₂R₃-but-3-ene-1-oic acid comprises treating a compound of formula $I_A$ to obtain a compound of formula $I_B$, reacting the latter with an acid agent capable of hydrolyzing the ketal group to obtain a compound of the formula

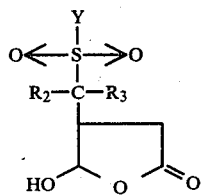

IV and reacting the latter with a basic agent to obtain a 3-formyl-4-R₂R₃-but-3-ene-1-oic acid.

The preferred acid hydrolysis agent is a strong acid selected from the group consisting of sulfuric acid, hydrochloric acid and p-toluene sulfonic acid and the acid is used in an aqueous acetone medium. The preferred basic agent is an alkali metal carbonate.

3-formyl-4-R₂R₃-but-3-ene-1-oic acid is used to prepare compounds of the formula

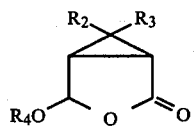

V wherein $R_4$ is hydrogen or the remainder of an alcohol of the formula $R_1OH$ as described in U.S. patent application Ser. No. 153,338 referred to above.

In the following examples there are described several preferred embodiments to illustrate the invention. However, it should be understood that the invention is not intended to be limited to the specific embodiments.

EXAMPLE 1

3-formyl-4-methyl-pent-3-ene-1-oic acid

STEP A:
4-p-tolylsulfonyl-4-methyl-3-dimethoxymethyl-pentanenitrile 22.5 ml of a 1.75 M n-butyllithium in benzene solution were added with stirring at −20° to −30° C. to a mixture of 7.9 g of p-tolyl isopropyl sulfone in 40 ml of tetrahydrofuran and after cooling the mixture to −60° to −70° C., a solution of 5 g of dimethylacetal of β-cyanoacrolein in 30 ml of tetrahydrofuran was added to the mixture. The mixture was stirred at −60° to −70° C. For 40 minutes, at −30° to −35° C. for 90 minutes and was then poured into an iced aqueous monosodium phosphate solution. The mixture was extracted with benzene and the organic phase was evaporated to dryness under reduced pressure. The residue was chromatographed over silica gel and was eluted with a 9-1 benzene-ethyl acetate mixture to obtain 8.33 g of 4-p-tolylsulfonyl-4-methyl-3-dimethoxy-methyl-pentanenitrile melting at 99° C.

IR Spectrum (chloroform):

Absorption at 2240 cm⁻¹ (—CN); at 1593-1490 cm⁻¹ (aromatic ring); at 1307-1295-1142 cm⁻¹ (—SO₂—).

NMR Spectrum (deuterochloroform):

Peaks at 1.35 ppm (geminal methyls); at 2.46 ppm (hydrogens of CH₃—of tolyl); at 2.75 ppm (hydrogens α- and β- to —CN); at 3.4 ppm (hydrogens of CH₃O—); at 4.7 ppm (hydrogen α- to CH₃O—); at 7.3 and 7.5 ppm (3- and 5- aromatic hydrogens of p-tolyl); at 7.7 and 7.9 ppm (2- and 6-hydrogens of p-tolyl).

STEP B:
4-p-tolylsulfonyl-4-methyl-3-dimethoxymethyl-pentanoic acid 4.98 g of the product of Step A were added to 200 ml of a 1-1 by volume ethanol-2 N aqueous sodium hydroxide solution mixture and the mixture was refluxed for 110 hours. The mixture was extracted with methylene chloride and the aqueous phase was acidified to a pH of 2 with oxalic acid. The acidified aqueous phase was extracted with methylene chloride and the organic phase was evaporated to dryness under reduced pressure to obtain 4.5 g of 4-p-tolylsulfonyl-4-methyl-3-dimethoxymethyl-pentanoic acid melting at 144° C.

IR Spectrum (Chloroform):

Absorption at 3510 cm⁻¹ (acid OH-monomer and dimere); at 1745 cm⁻¹ (carbonyl of monomeric acid); at 1711 cm⁻¹ (carbonyl of dimeric acid); at 1606 and 1425 cm⁻¹ (aromatic ring); at 1289-1148-1128 cm⁻¹ (—SO₂—).

NMR Spectrum (deuterochloroform):

Peaks at 1.31-1.36 ppm (geminal methyls); at 2.46 ppm (hydrogens of CH₃—of p-tolyl); at 2.66-3.08 ppm (hydrogens α- and β- to carboxyl); at 3.29-3.38 ppm (hydrogens of CH₃O—); at 4.4-4.46 ppm (hydrogen α- to CH₃O—); at 7.3-7.4 ppm (3- and 5-hydrogens of p-tolyl); at 7.75-7.9 ppm (2- and 6- hydrogens of p-tolyl).

STEP C: dl trans
4-(2-p-tolylsulfonyl-prop-2-yl)-5-hydroxytetrahydrofuran-2-one 1 g of the product of Step B was added to a mixture of 14 ml of acetone and 20 ml of aqueous N hydrochloric acid and the mixture was refluxed for 4 hours and was then extracted with methylene chloride. The organic phase was evaporated to dryness under reduced pressure to obtain 0.793 g of dl trans 4-(2-p-tolylsulfonyl-prop-2-yl)-5-hydroxy-tetrahydrofuran-2-one.

IR Spectrum (chloroform):

Absorption at 3580 cm⁻¹ (associated OH); at 1785 cm⁻¹ (carbonyl of γ-lactone); at 1595-1488 cm⁻¹ (aromatic rings); at 1310-1300-1125 cm⁻¹ (—SO₂—).

STEP D: 3-formyl-4-methyl-pent-3-ene-1-oic acid 0.788 g of the product of Step C was added to a solution of 20 ml of water and 2.4 ml of methanol and 0.790 g of sodium carbonate were added with stirring at −5° C. to the resulting mixture. The mixture was stirred at 20° C. for 2 hours and was extracted with ether. The aqueous phase was acidified to a pH of 3.5 by addition of 1 N aqueous hydrochloric acid. The mixture was extracted with chloroform and the organic phase was evaporated to dryness under reduced pressure to obtain 0.310 g of 3-formyl-4-methyl-pent-3-ene-1-oic acid melting at 102° C.

NMR Spectrum (deuterochloroform):

Peaks at 2.0 and 2.26 ppm (methyls); at 3.38 ppm (2-hydrogens); at 10.13 ppm (hydrogen of formyl).

EXAMPLE 2

3-formyl-4-methyl-pent-3-ene-1-oic acid

STEP A: Methyl 4-p-tolylsulfonyl-4-methyl-3-dimethoxymethylpentanoate 3.4 ml of a 1.95 M of butyllithium per liter of hexane were added at -70° C. to a mixture of 1.24 g of p-tolyl isopropyl sulfone in 13 ml of tetrahydrofuran and after stirring the mixture for 15 minutes, a solution of 1 g of methyl (E) 4,4-dimethoxy-2-butenoate in 20 ml of tetrahydrofuran was slowly added thereto. The mixture was stirred at −20° C. for one hour and was then poured into an aqueous monosodium phosphate solution. The mixture was extracted with methylene chloride and the organic phase was dried and evaporated to dryness under reduced pressure. The residue was chromatographed over silica gel and was eluted with an ether-petroleum ether (b.p. =40° to 70° C.) mixture to obain 1.1 g of methyl 4-p-tolylsulfonyl-4-methyl-3-dimethoxymethyl-pentanoate melting at 110° C.

IR Spectrum (chloroform):

Absorption at 1732 cm$^{-1}$ (carbonyl); at 1600 and 1495 cm$^{-1}$ (aromatic ring); at 1310-1301-1250 cm$^{-1}$ (—SO$_2$—); at 690 cm$^{-1}$

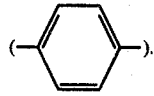

NMR Spectrum (deuterochloroform):

Peaks at 1.31-1.35 ppm (hydrogens of geminal methyls); at 2.45 ppm (hydrogens of CH$_3$— of p-tolyl); at 3.26-3.35 ppm (hydrogens of CH$_3$O—); at 3.6 ppm (hydrogens of CH$_3$OOC—); at 4.3-4.4 ppm (hydrogen α- to CH$_3$O—); at 7.3-7.4 ppm and 7.45-7.3 ppm (hydrogens of aromatic ring).

STEP B: 4-p-tolylsulfonyl-4-methyl-3-dimethoxymethyl-pentanoic acid 1 g of the product of Step A was added to a mixture of 20 ml of ethanol and 20 ml of aqueous 2 N sodium hydroxide solution and the mixture was refluxed for 17 hours and was cooled and poured into water. The mixture was extracted with methylene chloride and the organic phase was evaporated to dryness to obtain 4-p-tolylsulfonyl-4-(methyl-3-dimethoxymethyl-pentanoic acid.

STEP C: 3-formyl-4-methyl-pent-3-ene-1-oic acid

Using the procedure of Steps C and D of Example 1, the product of Step B was reacted to obtain 3-formyl-4-methyl-pent-3-ene-1-oic acid with the same constants as Example 1.

EXAMPLE 3 dl 6,6-dimethyl-4-hydroxy-3-oxa-bicyclo-[3,1,0]-hexan-2-one

STEP A: dl trans 4-(2-chloro-prop-2-yl)-5-hydroxy-tetrahydrofuran-2-one

A mixture of 1 g of the product of Example 2, 25 ml of ether and 1 g of dry lithium chloride was stirred under a current of gaseous hydrogen chloride at −30° C. for 2 hours and then at 0° C. for 2 hours after which the current of gaseous hydrogen chloride was stopped. The mixture was stirred at room temperature for 48 hours and after 54 hours of contact, the mixture was poured into iced water. The mixture was extracted with benzene and the organic phase was dried and evaporated to dryness under reduced pressure. The 1.1 g of residue was chromatographed over silica gel and was eluted with a 1-1 benzene-ethyl acetate mixture to obtain 545 mg of dl trans 4-(2-chloro-prop-2-yl)-5-hydroxy-tetrahydrofuran-2-one in the form of crystals melting at 80° C.

NMR Spectrum (deuterochloroform):

Peaks at 1.55 and 1.66 ppm (hydrogens of methyls); at 2.42 to 2.92 ppm (3- and 4-hydrogens of ring); at 5.82-5.89 ppm (5-hydrogen of ring); at 3.83 ppm (hydrogen of —OH).

STEP B: dl trans 4-(2-chloro-prop-2-yl)-5-[(3-phenoxyphenyl)-methoxy]-tetrahydrofuran-2-one A mixture of 393 mg of the product of Step A. 668 mg of m-phenoxybenzyl alcohol, 20 mg of p-toluenesulfonic acid and 5 ml of benzene was stirred at room temperature for 19 hours and was then neutralized with a little sodium bicarbonate. The mixture was dried and evaporated to dryness under reduced pressure. The 1.18 g of residue were chromatographed over silica gel and was eluted with benzene to obtain 467 mg of dl trans 4-(2-chloro-prop-2-yl)-5-[(3-phenoxyphenyl)-methoxy]-tetrahydrofuran-2-one which after crystallization from petroleum ether melted at about 50° C.

NMR Spectrum (deuterochloroform):

Peaks at 1.5 and 1.55 ppm (hydrogens of methyls); at 2.55-2.72 ppm (3- and 4-hydrogens of cyclopentyl): at 5.52-5.56 ppm (5-hydrogen of cyclopentyl); at 6.92-7.5 ppm (hydrogens of aromatic ring); at 4.47-4.66 ppm and 4.77-4.97 ppm (hydrogens of —CH$_2$—of benzyl).

STEP C: dl 6,6-dimethyl-4-hydroxy-3-oxa-bicyclo-[3,1,0]-hexan-2-one 0.25 ml of a solution of 2 M butyllithium in cyclohexane was added with cooling to -20° C. to 0.55 ml of a solution of 1 M of diisopropylamine in tetrahydrofuran and 5 ml of tetrahydrofuran and the temperature was allowed to rise to 0° C. The mixture was then cooled to −60° to −70° C. and 180 mg of the product of Step B were added thereto all at once. The mixture was stirred for 2 hours during which the temperature rose to 0° C. and the mixture was stirred at 0° C. for one hour and was poured into iced 2 N hydrochloric acid. The mixture was strongly stirred at 20° C. for 17 hours and the decanted aqueous phase was extracted with chloroform. The organic phase was dried and evaporated to dryness and the residue was added to a mixture of isopropyl ether and petroleum ether. The mixture was extracted with water and the aqueous phase was evaporated to dryness under reduced pressure to obtain 30 mg of dl 6,6-dimethyl-4-hydroxy-3-oxa-bicyclo-[3,1,0]-hexan-2-one in the form of crystals melting at 80° C.

Various modifications of the products and process of the invention may be made without departing from the spirit or scope thereof and it is to be understood that the invention is intended to be limited only as defined in the appended claims.

We claim:

1. A 3-formyl-4-methylpentanoic acid derivative of the formula

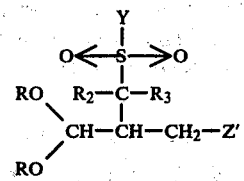

wherein Y is a monocyclic aromatic group selected from the group consisting of phenyl, tolyl and xylyl, $R_2$ and $R_3$ are individually alkyl of 1 to 4 carbon atoms or taken together with the carbon atom to which they are attached form a carbon homocycle of 3 to 6 carbon atoms, the Rs are alkyl of 1 to 6 carbon atoms or together form a polymethylene of 2 to 3 carbon atoms and Z' is selected from the group consisting of —COOH, cyano and —COOR$_1$ wherein R$_1$ is alkyl of 1 to 6 carbon atoms.

2. A compound of claim 1 wherein Z' is selected from the group consisting of —CN and —COOR$_1$ and R$_1$ is alkyl of 1 to 6 carbon atoms.

3. A compound of claim 1 wherein Z' is COOH.

* * * * *

UNITED STATES PATENT AND TRADEMARK OFFICE
CERTIFICATE OF CORRECTION

PATENT NO. : 4,382,037
DATED : May 3, 1983
INVENTOR(S) : JACQUES MARTEL ET AL.

It is certified that error appears in the above—identified patent and that said Letters Patent is hereby corrected as shown below:

Column 1, lines 25-30: Correct the formula to read

-- 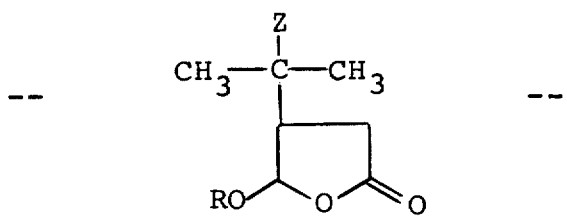 --

Column 3, line 56: "7.9 g" should read -- 7.79 g --.

Column 3, line 61: "For" should read -- for --.

Column 5, line 30: "dimethox-" should read -- dimethoxy- --.

Column 5, line 31: "ymethyl" should read -- methyl --.

Column 5, line 62: "4-(methyl-3-" should read -- 4-methyl-3- --.

Signed and Sealed this

Sixteenth Day of August 1983

[SEAL]

Attest:

GERALD J. MOSSINGHOFF

Attesting Officer   Commissioner of Patents and Trademarks